(12) United States Patent
Hoyos et al.

(10) Patent No.: US 9,170,186 B2
(45) Date of Patent: Oct. 27, 2015

(54) METHOD OF MANIPULATING OBJECTS

(75) Inventors: Mauricio Hoyos, Créteil (FR); Luz Angélica Castro Camacho, Paris (FR)

(73) Assignees: Centre National De La Recherche Scientifique, Paris (FR); Ecole Superieure De Physique Et De Chimie Industrielles De La Ville De Paris, Paris (FR)

( * ) Notice: Subject to any disclaimer, the term of this patent is extended or adjusted under 35 U.S.C. 154(b) by 570 days.

(21) Appl. No.: 13/489,555

(22) Filed: Jun. 6, 2012

(65) Prior Publication Data

US 2013/0327130 A1 Dec. 12, 2013

(51) Int. Cl.
*G01N 15/06* (2006.01)
*B01L 3/00* (2006.01)
*G01N 15/14* (2006.01)
*G01N 15/00* (2006.01)

(52) U.S. Cl.
CPC .......... *G01N 15/06* (2013.01); *B01L 3/502761* (2013.01); *B01L 2200/0668* (2013.01); *B01L 2400/0439* (2013.01); *G01N 2015/0038* (2013.01); *G01N 2015/142* (2013.01)

(58) Field of Classification Search
CPC ....................................................... G01N 15/06
USPC ............ 73/570.5; 181/0.5; 137/828; 436/174
See application file for complete search history.

(56) References Cited

U.S. PATENT DOCUMENTS 5,203,209 A * 4/1993 Watkins et al. ............... 73/570.5
5,665,605 A * 9/1997 Coakley et al. ............... 436/174

OTHER PUBLICATIONS

Bazou et al., "Controlled Cell Aggregation in a Pulsed Acoustic Field," Ultrasonics, 2012, vol. 52, No. 7, pp. 842-850.*
Martin et al., "Spore and micro-particle capture on an immunosensor surface in an ultrasound standing wave system", Biosensors and Bioelectronics 21 (2005), pp. 758-767.
Spengler et al., "Ultrasound conditioning of suspensions—studies of streaming influence on particle aggregation on a lab- and pilot-plant scale", Ultrasonics 38 (2000), pp. 624-628.
Coakley et al., "Analytical scale ultrasonic standing wave manipulation of cells and microparticles", Ultrasonics 38 (2000), pp. 638-641.
Hideto Mitome, "Ultrasonic Levitation and Accompanying Acoustic Streaming", Proceedings of 9th Symposium on Ultrasonic Electronics, Sendai 1988, Japanese Journal of Applied Physics, vol. 28 (1989) Supplement 28-1, pp. 146-148.
Spengler et al., "Microstreaming Effects on Particle Concentration in an Ultrasonic Standing Wave", AIChE Journal, Nov. 2003, vol. 49, No. 11, pp. 2773-2782.
N. Riley, "Steady Streaming", Annu. Rev. Fluid Mech. 2001. 33:43-65.

* cited by examiner

*Primary Examiner* — John Chapman, Jr.
(74) *Attorney, Agent, or Firm* — MH2 TECHNOLOGY LAW GROUP, LLP

(57) ABSTRACT

Systems, methods, and devices are provided for manipulating objects in a liquid using a pulsed acoustic field that is modulated in amplitude. The amplitude modulated pulsed acoustic field may form the objects into a layer or layers. The objects may be colloidal objects having an average size of about 50 nm to about 5 μm, or a mixture of colloidal and non-colloidal objects.

20 Claims, 12 Drawing Sheets

Pulsed mode
of operation

Continuous mode
of operation

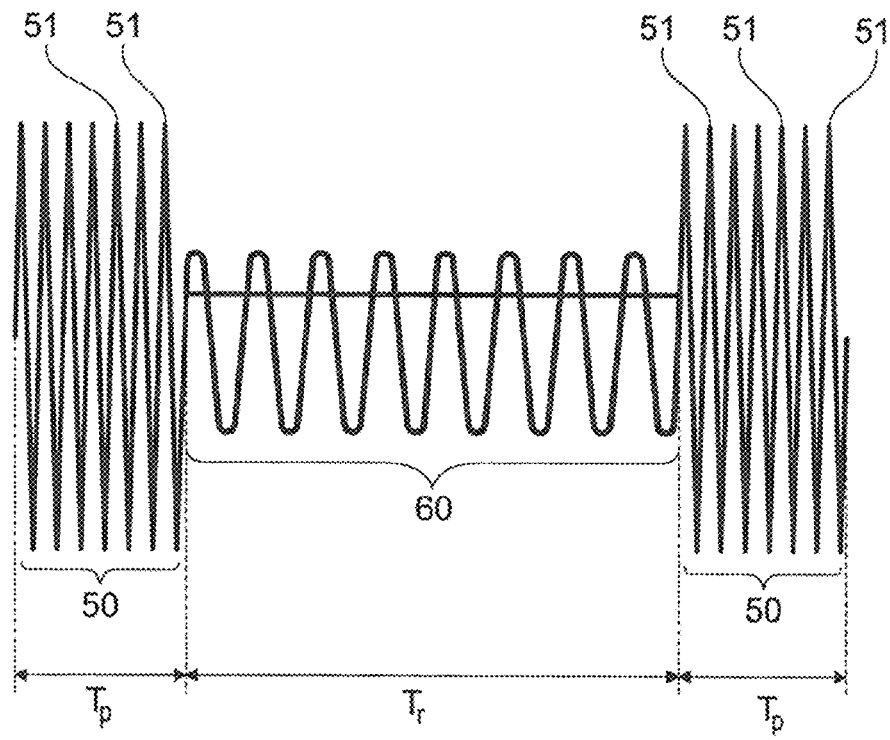
Fig. 5
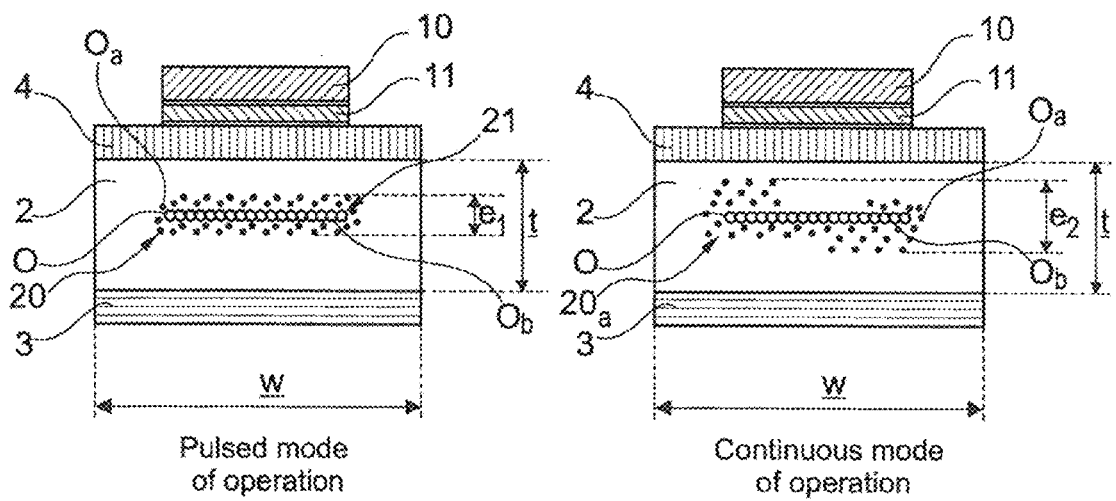
Pulsed mode of operation
Fig. 6
Continuous mode of operation
Fig. 7

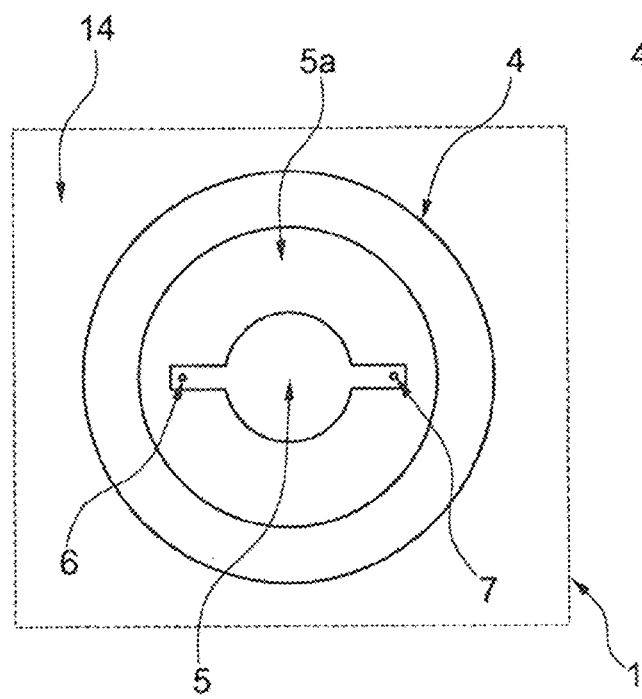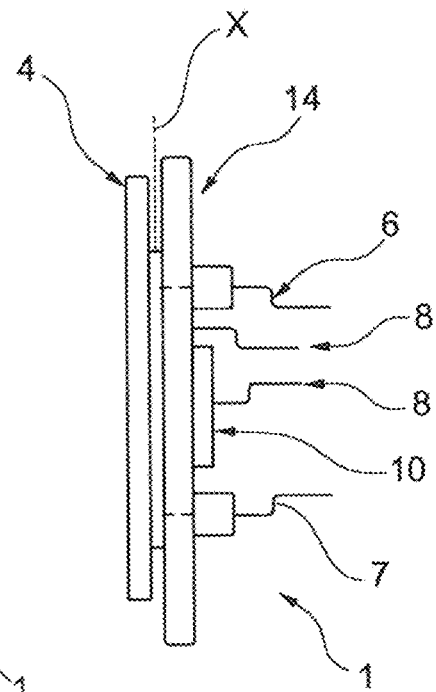
Fig. 11A  Fig. 11B
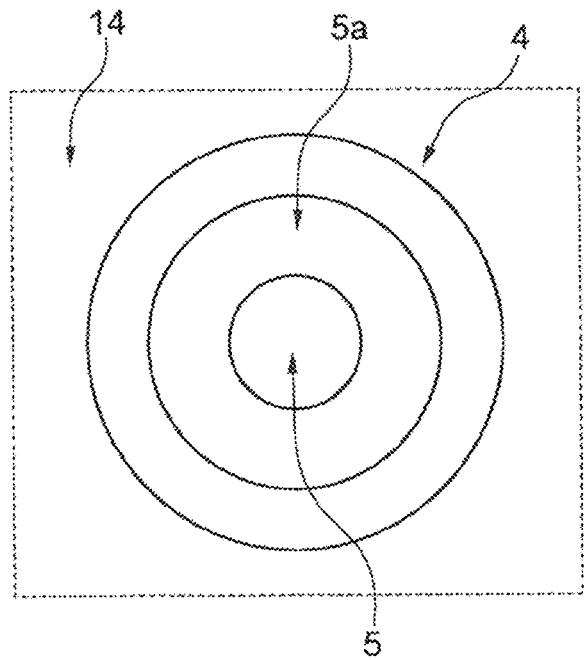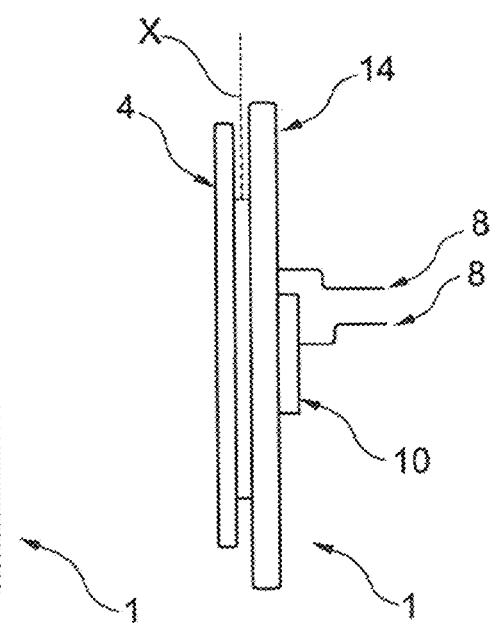
Fig. 11C  Fig. 11D

METHOD OF MANIPULATING OBJECTS

The present invention relates to methods of manipulating objects in a channel comprising a liquid.

BACKGROUND

Particle manipulation by using ultrasonic standing waves (USW) in microfluidic devices may commonly be used in bioseparations, characterization and analysis of micron-sized species.

A great number of publications highlighted the utility of USW by showing how particles, cells and bacteria can be affected by acoustic radiation forces.

Primary radiation forces may allow species to levitate at the nodal plane in a resonator. Inhomogeneity of the transversal energy distribution and non-idealities in geometry of the resonator may lead particles to agglutinate at the nodal plane and secondary Bjerknes forces may keep aggregates consolidated and stable.

Aggregation of cancer cells for instance can be generated in cylindrical resonators in order to study physiological cell interactions.

Species of a few micrometers or more may be trapped by using USW and can be focused at the nodal plane of a standing wave and kept closely immobile.

When species are smaller than a few micrometers, Brownian agitation may not be negligible and acoustic and thermodynamic forces may enter in competition for establishing a steady state after a relaxation time.

The acoustic streaming (corresponding to Rayleigh streaming in the present disclosure) may become observable when a suspension is composed of sub-micronic particles. In this case, the displacements of fluid may drag the species over the whole volume of the channel modifying thereby the thermodynamic equilibrium.

Several works have been devoted to the observation and description of the acoustic streaming in particle and cell manipulation and it was observed that acoustic streaming may generate clumps and recirculation of particles at nodal planes.

Acoustic streaming may be present when acoustic radiation pressure is generated by USW but primary radiation forces may veil it if size of objects is sufficient.

THE acoustic streaming can be visualized by using Particle Image Velocimetry (PIV) and it was shown that the flow velocity generated by the streaming may be strong enough for making manipulation of sub-micronic objects relatively difficult.

A need therefore exists to obtain a method allowing controlling the impact of the acoustic streaming, especially on relatively small objects.

A need also exists to obtain a method allowing reducing the impact of the acoustic streaming on objects while keeping acoustic forces strong enough for allowing a satisfying focusing of said objects.

The present invention aims to meet one or more of the aforementioned needs.

SUMMARY

According to a first aspect, the present invention concerns a method of manipulating objects in a channel comprising a liquid, said method comprising:
a) providing said objects in at least a region of the channel, and
b) forming a layer of said objects by submitting them to a modulated pulsed acoustic field, wherein the modulated pulsed acoustic field applied at step b) is modulated in amplitude and/or in frequency.

The present invention may advantageously provide means of controlling in a relatively easy manner the acoustic streaming.

The present invention may advantageously allow the application of increased acoustic forces on objects in comparison with the continuous mode of operation.

The present invention may advantageously allow the obtaining of a better acoustic focusing especially for objects which can be affected by the acoustic streaming in continuous mode of operation.

The present invention may advantageously allow the reduction of the acoustic field generator heating in comparison with the continuous mode of operation.

By "pulsed acoustic field modulated in amplitude" or "amplitude modulated pulsed acoustic field", it is meant a repetition of a plurality of acoustic wave pulse groups, said groups comprising a single or a plurality of acoustic wave pulses, when a group comprises a plurality of acoustic wave pulses, said pulses have, among this group, substantially the same amplitude and/or frequency, each of said groups being separated by one period having a non-zero duration wherein no acoustic wave is applied or wherein an acoustic wave is applied, said acoustic wave having at least one extremum of the absolute value of its amplitude that is different from the highest amplitude of the acoustic wave pulse(s) belonging to the group just preceding said period.

Unless contrary specified, by "amplitude", it is meant the mathematical function of evolution with respect to time of the value of a variable, e.g. of an acoustic wave.

According to the invention, a pulse is a portion of an acoustic wave presenting a maximum (i.e. a highest amplitude). In a group comprising a plurality of acoustic wave pulses, the pulses may be substantially identically repeated at substantially the same frequency of repetition. A group comprising a plurality of pulses may thus consist in a periodical repetition of pulses. In a variant, as mentioned above, the amplitude modulated pulsed acoustic field comprises a repetition of a plurality of acoustic wave pulse groups, all or part of said groups comprising, in particular consisting in, a single acoustic wave pulse. A pulse may be a portion of a sine curve, triangle-shaped or square-shaped.

The acoustic wave(s) applied during the period(s) may comprise, in particular consist of, a single or a plurality of acoustic wave pulses.

In the particular case wherein the modulated pulsed acoustic field applied at step b) comprises a succession of acoustic wave pulse sets, each of said set comprising, in particular consisting in, a single pulse or a plurality of pulses having the same amplitude and/or frequency, the first acoustic wave pulse group corresponds to the first acoustic wave pulse set applied to the objects during step b). Thus, in this particular example, the first period separating two groups corresponds to the second acoustic wave pulse set applied.

The manipulated objects may comprise colloidal objects.

According to the invention, the expression "colloidal objects" means objects aggregated or not when manipulated which have an average size comprised between 50 nm and 5 µm when isolated (i.e. not aggregated).

By "average size", it is meant the statistical granulometric dimension at the half of the population, known as D50.

In a preferred embodiment, one or more colloidal aggregates are manipulated during step b).

The expression "colloidal aggregate" means an aggregate of colloidal objects, the expression "aggregate" is hereunder defined.

In a preferred embodiment, the manipulated objects comprise a mixture of colloidal and non-colloidal objects. The non-colloidal objects may be micron-sized objects having an average size greater than 5 µm, e.g. greater than 5 µm and less than or equal to 50 µm.

An aggregate of objects, in particular of micron-sized objects, may be obtained during all or part of step b).

By "aggregate of objects", it is meant a layer of objects satisfying all of the following features:
- at least two objects comprised in said layer, in particular at least 10%, better 25%, preferably 50% of the objects comprised in said layer, are in contact, and
- said layer presents, on at least a portion of its length, a succession of objects when displacing along at least one of its transverse dimensions.

An aggregate may comprise, in particular consist in, juxtaposed rows of objects. In this case, the aggregates are referred to as 2D-aggregates. A 2D-aggregate may extend in a plane.

An aggregate may comprise a stacking of 2D-aggregates. Such an aggregate is an example of a 3D-aggregate.

An aggregate is different from a line of objects which only extend along an axis. In other words, a line of objects comprises only one object in width, only one object in thickness and a succession of objects along its length. A stacking of a 2D-aggregate and of a line of objects is another example of a 3D-aggregate.

Step b) may allow the formation of an aggregate of objects which have a size of 1 µm or more, for example 1 mm or more.

By "size of the aggregate of objects", it is meant its greatest dimension.

The formed aggregate may not settle down during step b).

Modulated Pulsed Acoustic Field

Acoustic Wave Pulse Groups

In an embodiment of the invention, at least one, in particular each, acoustic wave pulse group comprises 5 or more, preferably 10 or more, preferably 25 or more, preferably 50 or more, preferably 100 or more, acoustic wave pulses.

In an embodiment of the invention, at least one, preferably at least 25%, preferably at least 50%, preferably at least 75%, preferably the totality, of the acoustic wave pulse groups lasts a duration $T_p$ that is greater than or equal to 0.1 µs.

Step b) may comprise submitting the objects to at least 50, for example 100, for example 500, for example 1000, for example 5000, for example 10000, for example 25000, for example 50000, acoustic wave pulse groups.

The highest amplitude of the pulse(s) in all or part of the groups is preferably greater than the temporal average of the absolute value of the amplitude of the acoustic wave(s) applied during the period(s).

The temporal average of the absolute value of the amplitude of the acoustic wave(s) applied during the period(s) may be less than or equal to 50%, preferably less than or equal to 25%, more preferably less than or equal to 10%, of the highest amplitude of pulse(s) in the group just preceding the considered period(s).

The highest amplitude of pulse(s) in all or part of the groups may be greater than the highest amplitude of the acoustic wave(s) applied during the period(s).

As detailed below, it is preferable that the acoustic wave pulse groups are separated during step b) by period(s) wherein no acoustic wave is applied.

The acoustic wave pulses belonging to two successive groups comprising a plurality of pulses and separated by at least one period preferably have substantially the same amplitude and frequency. In other words, the acoustic wave pulses belonging to two different groups applied at step b) preferably have substantially the same amplitude and frequency.

In an embodiment, the acoustic wave pulse groups are periodically spaced between each other by a period having a non-zero duration.

Period(s) Separating the Acoustic Wave Pulse Groups

In a preferred embodiment, the acoustic wave pulse groups are separated between each other by a period having a non-zero duration wherein no acoustic wave is applied.

In a variant, it is also possible that the acoustic wave pulse groups are separated between each other by a period having a non-zero duration wherein an acoustic wave is applied, e.g. having a highest amplitude that is different, e.g. less, than the highest amplitude of the acoustic wave pulse(s) present in the group just preceding said period.

In an embodiment, at least one period, for example at least 25% of the periods, for example at least 50% of the periods, for example at least 75% of the periods, for example the totality of the periods, separating two successive acoustic wave pulse groups has a duration $T_r$ that is greater than or equal to 0.05 ms, preferably 0.1 ms, more preferably to 0.2 ms.

In an embodiment, at least one period, for example at least 25% of the periods, for example at least 50% of the periods, for example at least 75% of the periods, for example the totality of the periods, separating two successive acoustic wave pulse groups has a duration $T_r$ that is less than or equal to 0.5 s, preferably to 0.1 s, more preferably to 0.01 s, more preferably to 0.005 s.

Pulse Mode Factor

In an embodiment, at least a couple, for example at least 25% of the couples, for example at least 50% of the couples, for example at least 75% of the couples, for example the totality of the couples, of consecutive acoustic wave pulse group of duration $T_p$ and period separating two successive acoustic wave pulse groups of duration $T_r$ has a pulse mode factor $$P_{mf} = \frac{T_p}{T_p + T_r}$$

that is greater than or equal to 0.01, preferably 0.025, more preferably 0.1.

In an embodiment, at least a couple, for example at least 25% of the couples, for example at least 50% of the couples, for example at least 75% of the couples, for example the totality of the couples, of consecutive acoustic wave pulse group of duration $T_p$ and period separating two successive acoustic wave pulse groups of duration $T_r$ has a pulse mode factor $$P_{mf} = \frac{T_p}{T_p + T_r}$$

that is less than or equal to 0.95, preferably 0.75, more preferably 0.5.

In an embodiment, at least two couples of consecutive acoustic wave pulse group of duration $T_p$ and period separating two successive acoustic wave pulse groups of duration $T_r$ have a different pulse mode factor $$P_{mf} = \frac{T_p}{T_p + T_r}.$$

In an embodiment, all the couples of consecutive acoustic wave pulse group of duration $T_p$ and period separating two successive acoustic wave pulse groups of duration $T_r$ have substantially the same pulse mode factor $$P_{mf} = \frac{T_p}{T_p + T_r}.$$

Of course, the present invention also encompasses embodiments wherein the modulated pulsed acoustic field applied at step b) is modulated in amplitude and in frequency.

Adaptation Of the Modulated Pulsed Acoustic Field

In an embodiment at least one feature of the objects is measured and the modulated pulsed acoustic field applied in step b) is determined, in particular modified, in function of this measure.

The measured feature may be the average size of the objects.

Acoustic Field Generator and Acoustic Waves

In a preferred embodiment, a standing acoustic wave is created along a dimension, preferably along the thickness, of the channel at step b) during the application of the modulated pulsed acoustic field. The thickness may be less than the width of the channel. The thickness may be the smallest dimension of the channel.

The frequency of all or part of the acoustic wave pulses present in the acoustic wave pulse groups applied at step b) may be of 10 MHz or less, preferably comprised between 0.5 and 10 MHz.

The frequency of a single pulse defining an acoustic wave pulse group is equal to the inverse of its duration.

The use of an acoustic field generator in such ranges of frequency may advantageously facilitate maintenance of the integrity of living cells or objects such as vesicles, liposomes, bacteria or viruses.

The modulated pulsed acoustic field used at step b) may advantageously be generated along a thickness of the channel.

The acoustic field generator may be a piezoelectric, e.g. ceramic.

It is for example possible to use an acoustic field generator sold under the reference PZ26 by the company Ferroperm Piezoceramics, Kvistgard, Denmark.

The acoustic field generator may be digitally or analogically controlled.

The acoustic field generator may be powered by a wave generator for example the model 5062 sold by Tabor electronics, Israel.

The wave emitted by the wave generator may be amplified by an amplifier, such an amplifier is for example the model 9250 sold by Tabor electronics, Israel.

The wave generator may, during step b), generate waves having an amplitude of 40 Vp-p (Volts peak to peak) or less, e.g. of 20 Vp-p or less.

The acoustic energy density generated during all or part of step b) may be comprised between 1 and 2000 J/m³ (Joules/m³), for example between 1 and 300 J/m³, for example between 5 and 50 J/m³, and may for instance be of 10 J/m³.

The frequency of all or part of the acoustic wave pulses present in the acoustic wave pulse groups applied at step b) may be a resonant frequency of the channel along one of its dimensions, in particular along one of its transverse dimensions.

The transverse dimensions of the channel are the thickness and the width of the channel, when the channel is elongated along a longitudinal axis.

By "frequency which is a resonant frequency of the channel along one of its dimensions", it is meant a frequency $f_0$ such that a dimension z of the channel, measured at a given position along an axis of the channel transverse to this dimension, satisfies $$z = \frac{n\lambda}{2}$$

where n is an integer, and $$\lambda = \frac{c_f}{f_0}$$

where $c_f$ is the sound velocity in the liquid present in the channel at the temperature of said liquid, for example 20° C.

In other words, the frequency $f_0$ corresponds to the theoretical frequency satisfying, at a given position along an axis of the channel, the resonance condition of the acoustic wave in the channel and the formation of a stationary wave along the considered dimension.

The frequency of all or part of the acoustic wave pulses present in the acoustic wave pulse groups applied at step b) may be comprised between $0.5f_0$ and $1.5f_0$, in particular between $0.75f_0$ and $1.25f_0$.

The acoustic field generator may be fastened to one of the walls of the channel. This fastening may be done using any means known to the skilled artisan as appropriate, in particular by gluing.

A layer of an acoustic adaptation material may be present between the acoustic field generator and at least one of the walls of the channel.

The acoustic adaptation may be made by the use of any appropriate material known to the skilled artisan.

A plurality of acoustic field generators may be present along the length of the channel for generating said modulated pulsed acoustic field at step b), the acoustic field generators preferably being present on the same side of the channel.

In a variant, the acoustic field generators are present at opposite sides of the channel.

Channel

It is possible to use channels that are described in US 2008/0067128, the content of which is hereby incorporated by reference.

Geometric Features

The width and/or thickness of the channel may vary, optionally decrease, on at least a portion of its length.

Thus, when moving along the longitudinal axis of the channel, the thickness of said channel may be constant or may vary. The channel may in particular comprise at least two zones that axially follow one another and that present different thicknesses.

The channel may present, on at least a portion of its length, in particular on the totality of its length, a thickness that is less than or equal to 3 cm, better less than or equal to 1 cm. The channel is, for example, a micro-channel.

By "micro-channel", it is meant a channel having, over the totality of its greatest dimension, in particular of its length, a thickness that is less than or equal to 1 mm.

The channel may present on at least a portion of its length, in particular over the totality of its length, a thickness comprised between 50 µm and 3 mm, preferably between 100 µm and 500 µm.

The width of the channel may, when moving along the longitudinal axis of said channel, be constant or vary. The channel for example presents two zones that axially follow one another and that present different widths.

By "longitudinal axis of the channel", it is meant the line interconnecting the centers of gravity of the cross-sections of the channel. The longitudinal axis of the channel may be straight or curvilinear and may be contained in a plane which can be a plane of symmetry for some or even all of the cross-sections of the channel.

In an embodiment, the channel width may vary and the channel may be of a pyramidal shape when observed from above. In this particular case, the acoustic field generators may be rectangular or not.

In a variant, the channel may, when observed from above, have the shape of circles connected by sub-channels, in particular rectilinear sub-channels.

In the latter configuration, the acoustic field generators may be cylindrical.

The channel may have over at least a portion of its length, in particular over the totality of its length, a width comprised between 1 mm and 40 mm, preferably between 3 mm and 20 mm.

The length of the channel, measured along its longitudinal axis, is, for example, comprised between 3 mm and 1000 mm, preferably between 10 mm and 500 mm.

The channel may comprise a transversal section that is substantially constant when displacing along its longitudinal axis.

The channel may have over at least a portion of its length, in particular over the totality of its length, a rectangular transversal section.

In a variant, the channel may have over at least a portion of its length, in particular over the totality of its length, a square or circular transversal section.

The channel may advantageously have, over at least a portion of its length, a ratio of width/thickness and/or length/thickness that is greater than or equal to 10.

Such ratios may advantageously prevent three-dimensional effects in the flow profile.

In a preferred embodiment, the channel has, over at least a portion of its length, in particular over the totality of its length, a rectangular transversal section and a ratio width/thickness$\geq$10.

In an embodiment, the channel may have a length that is less than one or both of its transverse dimensions.

The channel may be cylindrical shaped, its diameter being greater than its height. In this example, the diameter of the channel may be comprised between 1 and 20 mm and/or the height may be comprised between 50 µm and 3 mm.

Walls of the channel may be platelet-shaped.

Walls of the channel may have over at least part, in particular the totality, of their length a thickness comprised between 0.1 mm and 5 mm.

The channel may comprise, over at least a portion of its length, a wall whose thickness varies.

The wall opposite to the wall wherein the acoustic field is generated may freely oscillate when the method according to the invention is carried out.

Inlet(s) and Outlet(s)

The channel may be in fluidic communication with at least one inlet.

The channel may be in fluidic communication with at least one outlet.

The channel comprising an inlet and/or outlet may be placed in a stable frame. The channel inlet(s) and/or outlet(s) may be connected to syringe pumps and/or peristaltic pumps. When they are connected to peristaltic pumps, a hydrodynamic dampener may be added between the peristaltic pump and the channel inlet(s) and/or outlet(s).

The channel may be in fluidic communication with one or more outlet(s) where objects may be evacuated.

As such, it may not be necessary to open the channel in order to collect the objects.

At least one of the inlet(s) may present a width that is not less than the width of the channel and/or may present a section that is substantially rectangular.

At least one inlet may open out into the channel substantially parallel to or perpendicular to the longitudinal axis thereof.

In an embodiment of the invention, at least one feed orifice is in fluidic communication with at least one the inlet(s) via a duct, the duct including in particular a diverging portion that diverges from a tip of the duct, the feed orifice opening out into the duct adjacent to said tip, and in particular perpendicularly to the duct.

This diverging portion of the duct makes it possible to form a sheet of substance starting from a feed point.

In an embodiment of the invention, at least one outlet orifice is in fluidic communication with the outlet(s) of the channel via a duct, the duct includes a portion of section that narrows laterally, in particular a portion converging towards a tip, said portion being triangular in shape when observed from above, for example, the outlet orifice opening out into the duct, e.g. adjacent to the tip, and in particular perpendicularly to the duct.

This converging portion of the duct may serve to avoid formation of a stagnation point at the outlet orifice.

Materials Constituting the Channel

The walls of the channel may comprise, in particular consist of, a material chosen among: organic or mineral glasses, quartz, thermoplastic materials, in particular PMMA or polycarbonate, and metals. More generally, all or part of the walls of the channel may comprise, in particular consist of, a material having a high acoustic impedance, i.e. at least ten times greater than the acoustic impedance of the fluid.

The channel may be fabricated using conventional fabrication methods of the kind used in the field of microfluidics.

Where appropriate, the microchannel may be provided with at least one valve, e.g. a solenoid valve.

Liquid and Objects

The liquid may be a biological liquid such as blood.

In a variant, the liquid may be water.

The liquid may be transparent to visible light.

The liquid may not be flowing during step b).

According to an embodiment, the liquid is flowing during step b), the Reynolds number of the flow of the liquid optionally being less than 10.

The objects may be monodisperse or polydisperse biological cells, in particular blood cells.

The objects may be rigid or deformable particles, for example polystyrene particles.

More generally, the objects may be rigid or deformable particles, polydisperse particles, biological cells, in particular blood cells, e.g. cancer cells in a blood sample, bacteria, colloidal or non-colloidal emulsions, proteins or liposomes.

The objects may be mono or polydisperse biological cells, preferably mammalian tumor or non-tumour cell line, stem cells or primary cell lines.

The manipulated objects may comprise colloidal objects as mentioned above.

The flow rates used may depend on the samples treated, the channel volume and the acoustic forces applied.

For instance, the liquid may be flowing during all or part of the method according to the invention at a flow rate comprised between 0.01 ml/min to 100 ml/min.

The volume fraction of objects, measured when said objects are injected in the channel, may be 0.1% (v/v) or more. The volume fraction of objects corresponds to the [(volume of objects)/(volume of liquid containing said objects)]×100%.

BRIEF DESCRIPTION OF THE DRAWINGS

The invention will be better understood from a reading of the detailed description below, of non-limiting examples for its implementation, and from examination of the attached drawings, in which:

FIGS. 4 and 5 show examples of modulated pulsed acoustic fields for carrying out a method according to the invention, FIG. 6 shows a layer of objects obtained by a method according to the invention, FIG. 7 shows a layer of objects obtained in continuous mode of operation, FIGS. 11A to 11D show examples of structures of resonator that can be used for carrying out a method according to the invention.

DETAILED DESCRIPTION

Figure 1:
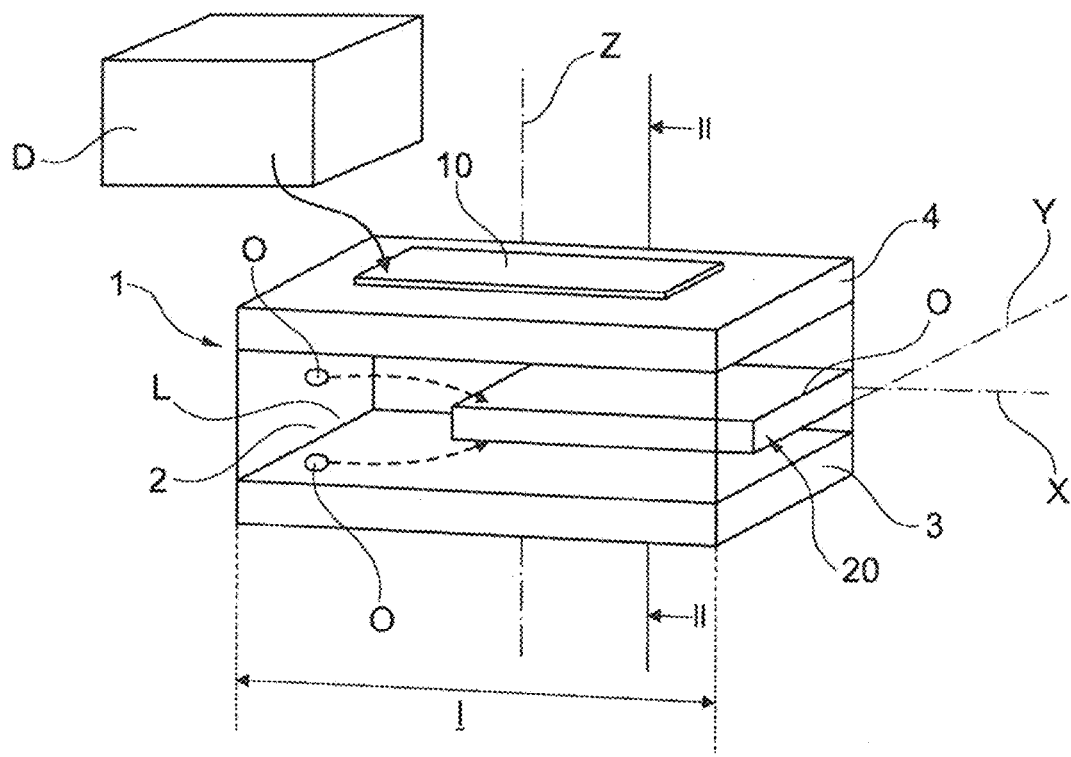
FIG. 1 shows a device for carrying out of a method according to the invention.

FIG. 1 shows a device 1 which may be used in the methods according to the invention. The device 1 comprises a channel 2 extending along a longitudinal axis X.

The channel 2 may, as mentioned above, be a microchannel.

The channel 2 may present a cross-section that is rectangular. In the example described, the length/thickness ratio of the channel 2 is greater than 10.

The channel 2 has bottom and top walls 3 and 4. As shown in FIG. 1 for example, a carrier liquid L and a plurality of objects O are present in the channel 2.

Objects O may be mono or polydisperse, said objects O may be biological cells and liquid L may be a biological liquid such as, e.g. blood.

Objects O may comprise colloidal objects and/or colloidal aggregates (i.e. aggregates of colloidal objects).

The injection of objects O in the channel 2 can be controlled in frequency and in flow rate so as to enable the device 1 to operate continuously in order to process large volumes of objects.

The device 1 is further provided with an acoustic field generator 10 which is, as shown, fastened to the top wall 4 of the channel 2. The acoustic field generator 10 enables formation, at step b), of a layer 20 of objects O by submitting them to a modulated pulsed acoustic field.

As shown in FIG. 1, the layer 20 is in levitation around a pressure node or anti-node of the waves generated by the acoustic field generator 10. The modulated pulsed acoustic field produced by the acoustic field generator 10 may allow the formation of a standing acoustic wave along the thickness of the channel 2 (Z-axis). The layer 20 is as shown in FIG. 1 not in contact with the walls 3 and 4 during step b).

The expression "acoustic levitation" is employed when acoustic manipulation seeks to place objects in an equilibrium position against gravity. The equilibrium position depends on the acoustic properties of the objects and the suspending liquid, the acoustic power and the position and number of nodes of the acoustic waves.

The acoustic field generator 10 may be supplied by a signal from a generator D which e.g. comprise a wave generator connected to an amplifier. The generator D may supply the acoustic field generator 10 with groups of sine-shaped voltage pulses. In a variant, the acoustic field generator 10 may be supplied by the generator D with groups of triangular-shaped or square-shaped voltage pulses.

Figure 2:
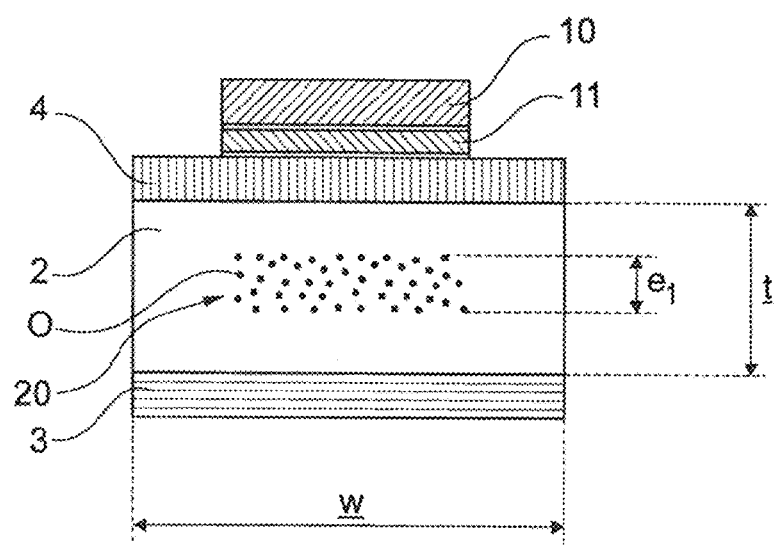
FIG. 2 is a view according to II-II of the channel used in FIG. 1.

As shown in FIG. 2, a layer of a gel 11 acting as an acoustic impedance adapter may be present between the acoustic field generator 10 and the top wall 4 of the channel 2.

The layer 20 obtained by submitting objects O to the modulated pulsed acoustic field may have a dimension $e_1$ measured along the axis of application of the acoustic waves, which corresponds in the illustrated case to its thickness, comprised between $50\,d_{av}$ and $150\,d_{av}$ where $d_{av}$ is the average size of the objects O when individualized (i.e. not aggregated).

The dimension $e_1$ measured along the axis of application of the acoustic waves may be determined by quantifying the number of objects in function of the position along this axis as performed in FIG. 7 of Dron et al. (Microfluid Nanofluid (2009) 7:857-867), the content of which is incorporated by reference The measurements are done in steady state, the liquid not be flowing. The dimension $e_1$ is determined by subtracting the values of the two positions which define a zone comprising the pressure node or anti-node around which the layer is in levitation and comprising at least 90%, preferably 95% of the objects.

Figure 3:
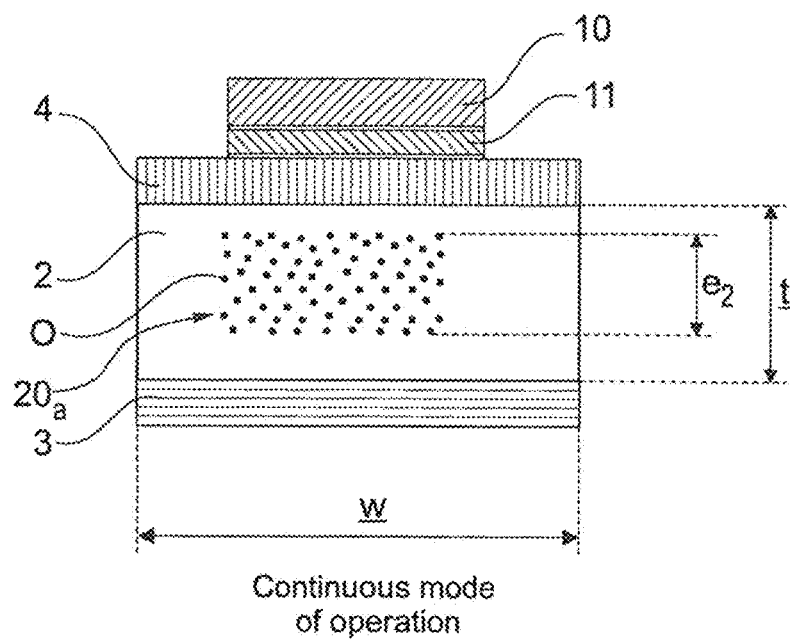
FIG. 3 shows a layer of objects obtained by a continuous mode of operation.

FIG. 3 shows a layer of objects $20_a$ obtained in continuous mode thus not by submitting objects to a modulated pulsed acoustic field. All things being equal, the layer $20_a$ obtained in continuous mode may have a dimension $e_2$ measured along the axis of application of the acoustic waves, which corresponds in the illustrated case to its thickness, greater than the dimension $e_1$ (see FIGS. 2 and 3).

More particularly, the ratio $$\frac{e_1}{e_2}$$

may be comprised between 0.2 and 0.8.

Figure 4:
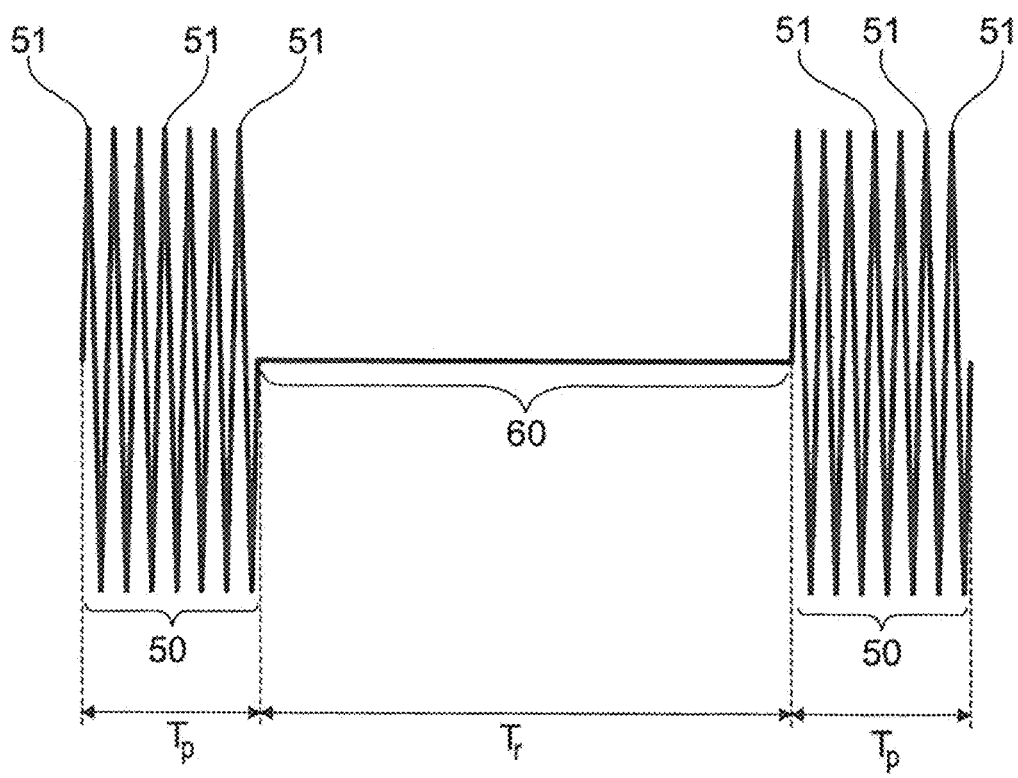

FIG. 4 shows an example of a temporal evolution of a signal corresponding to a pulsed acoustic field modulated in amplitude which may be used in step b) according to the invention.

The modulated pulsed acoustic field may as shown comprise a repetition of a plurality of acoustic wave pulse groups 50. The groups 50 may comprise, as shown, a plurality of acoustic wave pulses 51, said pulses 51 having, among a given group 50, substantially the same amplitude and frequency, and said groups 50 being separated between each other by a period 60 having a non-zero duration wherein no acoustic wave is applied.

Each of the acoustic wave pulse groups 50 may comprise 5 or more, preferably 10 or more, preferably 25 or more, preferably 50 or more, preferably 100 or more, acoustic wave pulses 51.

The totality of the acoustic wave pulse groups 50 may last a duration $T_p$ that is greater than or equal to 0.1 µs.

The totality of the periods 60 separating two successive acoustic wave pulse groups 50 may have a duration $T_r$ that is greater than or equal to 0.05 ms, preferably 0.1 ms, more preferably to 0.2 ms.

The totality of the periods 60 separating two successive acoustic wave pulse groups 50 may have a duration $T_r$ that is less than or equal to 0.5 s, preferably to 0.1 s, more preferably to 0.01 s, more preferably to 0.005 s.

The present disclosure also encompasses the use of variants of modulated pulsed acoustic field wherein an acoustic wave is applied during a period separating two acoustic wave pulse groups.

Such an embodiment is shown in FIG. 5 wherein two successive acoustic wave pulse groups 50 are separated by a period 60 wherein an acoustic wave is applied. The acoustic wave applied during the period 60 has as shown a highest amplitude that is less than the highest amplitude of the acoustic wave pulses 51 of the groups 50.

As shown in FIG. 5, the temporal average of the absolute value of the amplitude of the acoustic wave applied during the period 60, said temporal average corresponding to the horizontal line drawn, is less than 50% and for example approximately equal to 25% of the highest amplitude of pulses 51 in the groups 50.

The present disclosure also encompasses the use of variants of modulated pulsed acoustic field wherein the pulses of a same group have substantially the same frequency but their amplitude vary. The groups may for example in this case be triangle or sine-shaped.

The present disclosure also encompasses the use of variants of modulated pulsed acoustic field wherein all or part of the groups consist in a single acoustic wave pulse.

FIG. 6 shows an embodiment of a method according to the invention wherein the objects O manipulated comprise a mixture of colloidal objects O, and micron-sized objects $O_b$, the micron-sized objects $O_b$ having an average size greater than the average size of the colloidal objects $O_a$.

The formed layer 20 of objects O may comprise an aggregate 21 of micron-sized objects $O_b$. Some colloidal objects $O_a$ may surround all or part of said aggregate 21 as shown in FIG. 6.

As shown, the colloidal objects $O_a$ and the micron-sized objects $O_b$ may during all or part of step b) be focused around a nodal plane, in particular around a same nodal plane.

FIG. 7 shows the result of a method consisting in submitting a mixture of colloidal $O_a$ and micron-sized objects $O_b$ to a continuous mode of operation.

The thickness of the layers of objects O obtained may be as described concerning FIGS. 2 and 3.

Figures 8, 10:
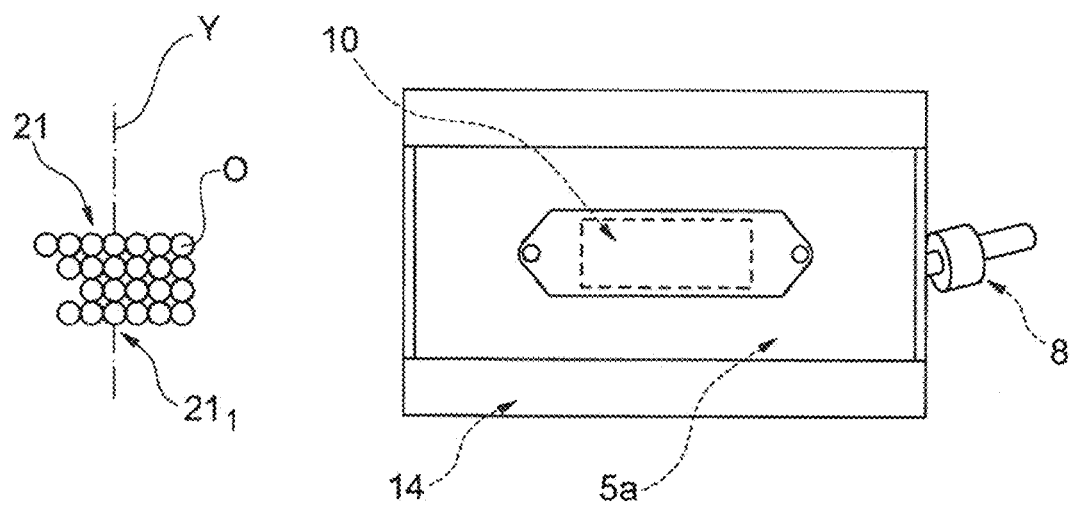
FIG. 8 shows an aggregate obtained according to a method of the invention.
FIG. 10 shows an example of structure of resonator that can be used for carrying out a method according to the invention.

As explained above, an aggregate of objects may be more compact than a layer of objects. FIG. 8 shows an upper view of an aggregate 21 obtained during step b) according to the invention. The aggregate 21 comprises a set of objects O that are in contact with each other, e.g. at least 50% of the objects O constituting said aggregate 21 can be in contact with each other.

The invention may enable the formation of 2D and/or 3D aggregates. The definition of such 2D and 3D aggregates is given below.

The aggregate 21 comprises a succession $21_1$ of objects O when moving along the Y axis which corresponds to a displacement along the width of the channel 2 but has a thickness formed of at least one object. In this case, the aggregate 21 is a 2D-aggregate.

In an embodiment, the aggregate also comprises a succession of objects O when moving along the thickness of the channel 2. The aggregate is thus a 3D-aggregate.

Figure 9:
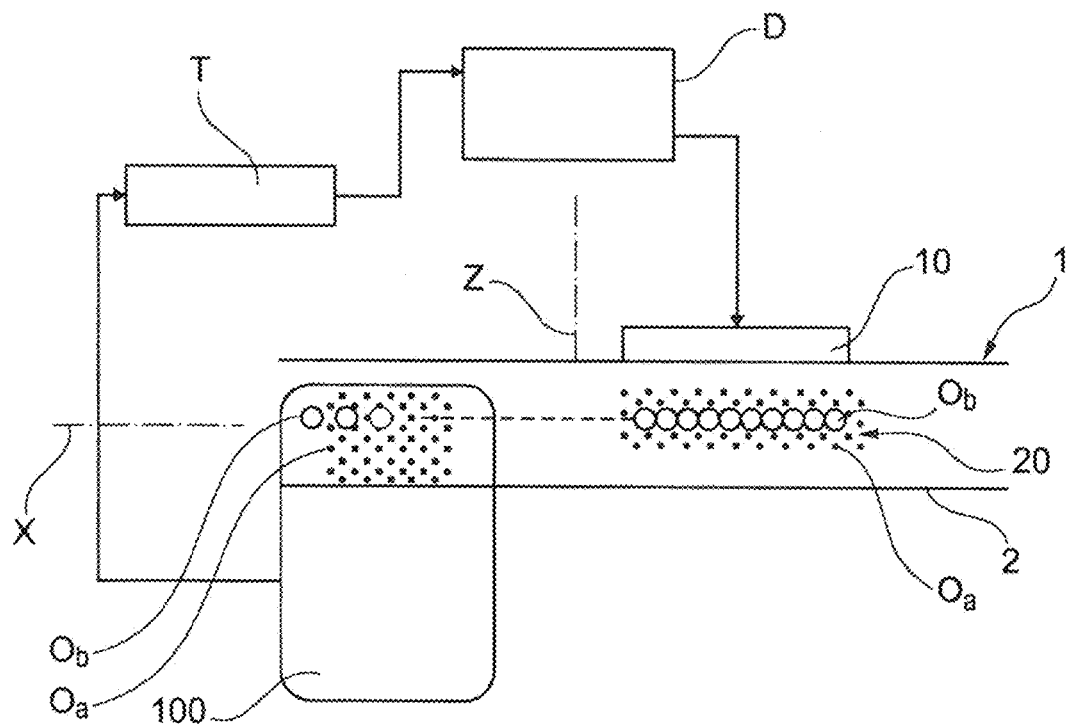
FIG. 9 shows another embodiment of device for carrying out of methods according to the invention.

FIG. 9 shows a variant of a device 1 for carrying out a method according to the invention.

In this embodiment, a device 100 is present and allows the measurement of at least one feature of the objects O. For example, the device 100 may detect the presence of colloidal objects $O_a$ or of a mixture of colloidal objects $O_a$ and micron-sized objects $O_b$.

The result of the measure carried out by the device 100 may be transmitted to a device T controlling the acoustic field applied in function of said measurement. The device T e.g. allows the application of a modulated pulsed acoustic field if colloidal objects $O_a$ are detected by the device 100 and thus may allow the creation of a layer 20 of objects.

Experimental Part
Experimental Set-Up

Experiments have been conducted in two different chambers in order to show that the control of the streaming is independent of the resonator geometry.

The first ultrasonic resonator UR1, was a Hele-Shaw cell of 4 cm length, 5 mm wide and 280 µm thickness, composed of 2 mm thick stainless steel plate 14 and 1 mm glass plate separated by a polyimide Kapton® tape spacer 5a assembled in sandwich with neoprene glue. A connector 8 is present to supply electric signal to the transducer 10.

The second ultrasonic resonator UR2, was a cylinder of 5 mm diameter and 180 µm height composed of a 2 mm thick stainless steel plate and 180 μm thick glass slide, separated by polyimide Kapton® tape. Two different examples of such a structure are shown in FIGS. 11A to 11D.

FIG. 11A shows a top view of the first example, FIG. 11B is a side view of the device of FIG. 11A, FIG. 11C is a top view of the second example and FIG. 11D is a side view of the device of FIG. 11C.

These structures have four layers, a transducer 10 (PZ26 Ferroperm, Kvistgard, Denmark) nominally resonant in the thickness mode at 2.25 MHz and mounted in a radially symmetric housing, a steel layer 14 coupling the ultrasound to a one half wavelength ($\lambda/2$, where $\lambda$ is the wavelength of sound in water at 2.13 MHz) aqueous layer and an acoustic reflector 4, e.g. made of quartz, that provided optical access from above.

A resonant cavity 5 is defined by a polyethylene terephtalate (Mylar®) or polyimide spacer 5a.

It is also possible to use an acoustic reflector made of a plastic material and/or to substitute the steel layer 14 by a layer made of quartz or a plastic material.

The size of the steel plate was comprised between 5 mm and 10 mm. The resonant cavity 5 may have a diameter comprised between 1 mm and 20 mm. The disc transducer (12 mm diameter) 10 was driven at 2.13 MHz The trap 1 shown in FIGS. 11A and 11B has one sample inlet 6 and one sample outlet 7. The traps 1 are further provided with connectors 8 for connection to a voltage generator. Each of the connectors 8 is electrically connected to a face of transducer 10. One of the connectors 8 is as shown in contact with the steel layer 14, electrical contact with the face of the transducer 10 fastened to the layer 14 is ensured by a layer of conductive epoxy (not shown).

The trap 1 shown in FIGS. 11C and 11D does not comprise any inlet or outlet.

We note that the nominal resonance frequency of the transducer 10 (2.25 MHz) is different than the nominal resonance frequency of the resonator (2.13 MHz) due to the steel-coupling layer 14. The acoustic reflector 4 may have a thickness of 0.5 mm, 1 mm or 2 mm and may be made of glass, in particular quartz glass.

The transducer was glued with conductive epoxy (Chemtronics ITW, Kennesaw Ga., USA) behind the metal plate in both chambers.

Ultrasounds have been generated by 100 MHz dual channel arbitrary wave generator (5062 Tabor Electronics, Israel), the signal was amplified by a dual differential wide band 100 MHz amplifier (9250 Tabor Electronics, Israel) and the signal was visualized with a digital storage oscilloscope (IDS 8064 60 MHz ISOTECh, Hanan-Israel).

We employed 800 nm latex particles (Fluorescent particles, Polysciences Inc, Warrington Pa., USA) of concentration by volume less than 0.1%. Some experiments have been performed with a mixture of 800 nm and 15 μm latex particles (Micromod Rostock-Warnermunde, Germany).

All the experiments were performed in steady state flow. The suspension has been observed by a reflecting Olympus epi-fluorescence microscope with magnifications 10× and 20× provided with a high resolution camera DCU223M Thor-Labs (Hans-Brocker, Dachau Germany). The results of the observation were recorded in a personal computer.

We used a resonance frequency of 2.63 MHz in the UR1 parallel plate channel resonator and a resonance frequency of 4.12 MHz in the UR2 cylindrical shaped resonator.

The maximum wave amplitude applied in both resonators was 13 Vp-p. Both resonators presented one pressure node close to the mid distance between the walls.

Example 1

Evidence of the Acoustic Streaming Control

The acoustic streaming was first studied in the UR1 device. When the acoustic field was off, 800 nm particles submitted to Brownian motion, were initially distributed in the whole channel thickness.

Once the acoustic field was applied, the 800 nm particles were both focused by the primary radiation force around the nodal plane and dragged out by the acoustic streaming.

After a period of relaxation, a quasi-steady state was observed into the microscope field of view, which was 210× 157 μm² at 10× magnification. The quasi-steady state was identified when the streaming velocity and the thickness of the layer formed by focused particles reached constant values. The relaxation time was estimated less than 45 s in our specific experimental conditions.

The microscope was focused in the thickness at the nodal plane, previously determined by the equilibrium position reached by 15 μm latex particles when the ultrasounds were applied at maximum amplitude.

The concentration profile showed an apparent higher 800 nm particle concentration at the nodal plane.

We determined the layer thickness by measuring the positions of the first and the last particles with the microscope. The precision of the measurement was relatively low in continuous mode at maximum amplitude because of the presence of the acoustic streaming. We reach better precision in pulsed mode when the acoustic streaming was the minimum observable; we shall discuss this aspect later on.

Figure 12:
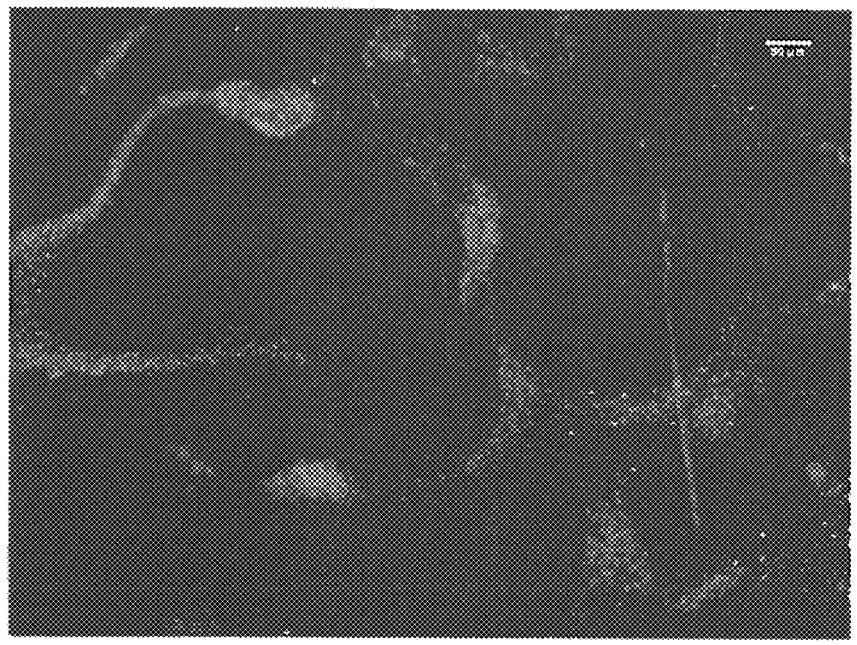
FIG. 12 shows acoustic streaming patterns of 800 nm fluorescent particles, magnification 5× observed in the resonator in continuous mode after 2 minutes of experiment.

We observed agglutination of particles and recirculation forming stretched clouds, as shown in FIG. 12.

These structures more or less stable have been formed several minutes after the acoustic force was applied. The meaning of "stable" is that the structure remains more or less unchanged even though particles continue to move agglutinating and following the streamlines in closed trajectories.

We fixed the observation zone in a location where the particle flux was roughly constant and the streaming velocity throughout the horizontal plane did not vary more than 20%. The streaming velocity considered was an average of particle velocities determined at three different points in the plane field of view.

When the ultrasounds were turned off, the flow stopped instantly while when the ultrasounds were turned on the streaming took some seconds to be established.

The acoustic streaming characteristic velocity has been determined by tracking both individual particles and small aggregates composed of a few particles and using the freeware software Tracker available at http://www.cabrillo.edu/~dbrown/tracker/.

Individual particles have been tracked when the microscope was operating in fluorescence mode.

The first experiment aimed at measuring the acoustic streaming characteristic velocity $v_{s,max}$ in continuous mode at maximum applied voltage.

Figure 13:
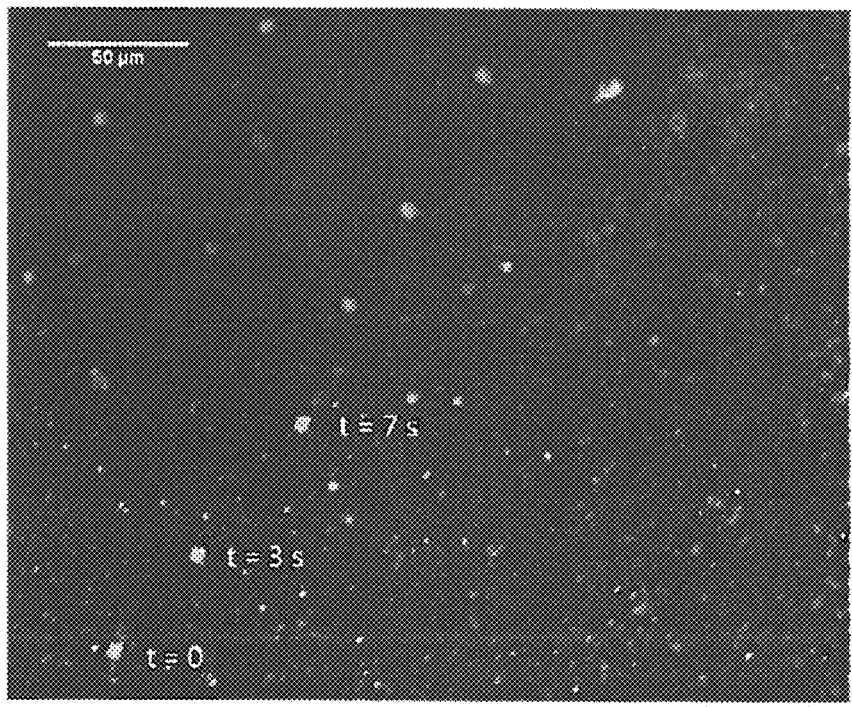
FIG. 13 shows superimposed images of an aggregate of 800 nm particles at the levitation plane (magnification 10×) at three different moments of the migration in continuous mode.

An example of tracking particles is depicted in FIG. 13 where a superposition of three images shows the displacement of a small aggregate composed of a few 800 nm particles during 7 s.

The average streaming velocity in this example was $v_{s,max}=15$ μm/s.

We noted that in many cases colloidal aggregates formed during the process of diameter bigger than ~10 μm moved at slower velocity than the bulk flow, until 30% of the streaming velocity. This is an important finding because a relative velocity between an object, in this case a colloidal aggregate, and the surrounding fluid means that the object may be manipulated by acoustics as done with rigid particles. We shall refer to this aspect later on.

In order to study the influence of pulsed ultrasounds on the acoustic streaming, we performed experiments measuring the streaming velocity (i.e 800 nm particle velocity) at different numbers of pulses $T_p$ (i.e in this example at different durations wherein the acoustic field is "on") and different repetition times $T_r$ (i.e in this example at different durations wherein the acoustic field is "off").

Figure 14:
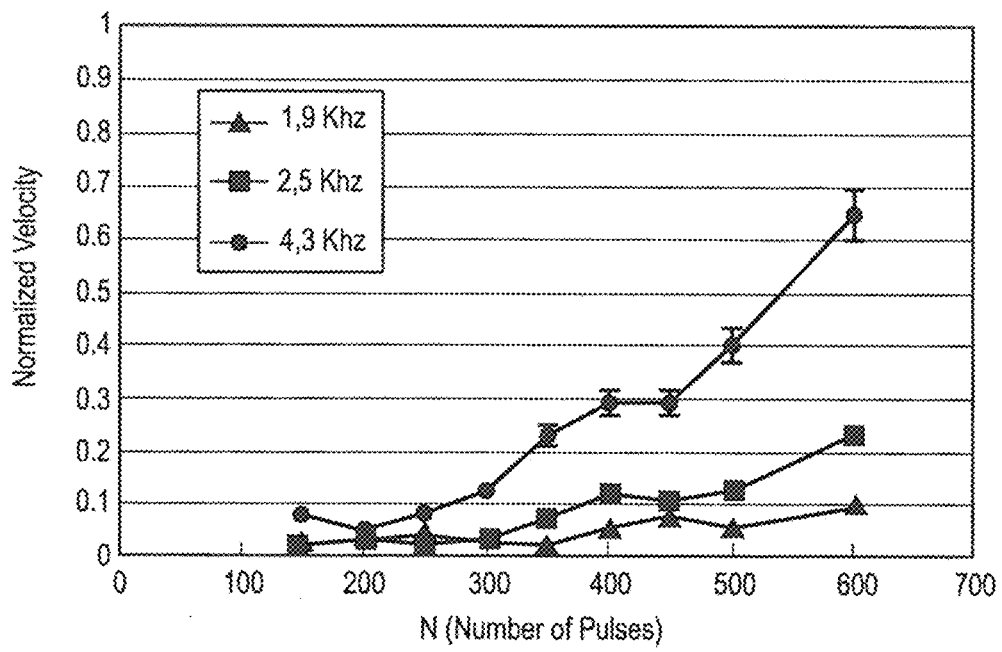
FIG. 14 shows the evolution of the normalized streaming velocity in function of the number of pulses for three different repetition frequencies.

In FIG. 14 is depicted the normalized streaming velocity $$\frac{v_s}{v_{s,max}}$$

in pulsed mode in function of the number of pulses N for three different repetition frequencies fr=1/$T_r$=1.9, 2.5 and 4.3 kHz.

At fixed repetition frequency, $v_s$ is a monotonically increasing function of the time of application of the ultrasounds and, at fixed number of pulses, $v_s$ is an increasing function of the repetition frequency.

This trend was expected, in fact, we assume that in mode "acoustic on" particles move at constant velocity during the time $T_p$ corresponding to the maximum streaming velocity $v_{s,max}$ and in "acoustic off" particles stop instantly. These curves show that we have two useful parameters for controlling the acoustic streaming in complementary manner.

The experiments detailed hereunder were performed to demonstrate that the pulsed mode allows diminishing the streaming in the resonator without inhibiting the possibility of manipulating micron-sized objects like particles or cells.

However, before referring to latter experiments, it is worthwhile to compare the performances of the pulsed mode with a continuous mode of operation wherein wave amplitude is reduced.

Example 2

Comparison Between Pulsed Mode and Continuous Mode with Reduced Amplitude

Other way of controlling the acoustic streaming could be to modify in continuous mode the wave amplitude given in Volts peak to peak (Vp-p).

Experiments performed in the UR1 device with 800 nm particles show, as expected, the streaming velocity increasing with the amplitude.

Nevertheless, in order to compare continuous and pulsed modes, we need to find common variables.

On the one hand, it is known that the acoustic energy is proportional to the square of the amplitude. On the other hand, the streaming velocity is proportional to the energy according to the relationship: $v_s=3\pi/32[v_0/c_0]^2 y_l f$ with $y_l$ the levitation plane distance from the bottom wall of the resonator, $c_0$ the sound speed in the fluid and f the frequency; $v_0$ is the amplitude of the ultrasonic velocity related to acoustic energy density by the relationship: $<Eac>=½\rho_0 v_0^2$.

We see therefore that the streaming velocity becomes proportional to the average energy density. The maximum streaming velocity $v_{s,max}$ is the velocity at the maximum voltage and is proportional to the maximum energy density $<Eac,max>$.

It follows that $v_s/v_{s,max}=<Eac>/<Eac,max>=(Vp-p/Vp-p,max)^2$.

In pulsed mode, we can make the hypothesis that the average particle velocity during one cycle is $$v_s = v_{s,max}\frac{T_p}{T_p + T_r} = v_{s,max}P_{mf},$$

where $P_{mf}$ is the pulse mode factor.

In continuous mode $P_{mf}=1$ and $P_{mf}=0$ when the acoustic force is "off".

Being proportional to the streaming velocity, $P_{mf}$ becomes thereby proportional to the mean energy density $<Eac>$. It follows that $v_s/v_{s,max}=<Eac>/<Eac,max>=P_{mf}/P_{mf,max}=P_{mf}$, with $P_{mf,max}=1$. Pulsed and continuous modes are compared in FIG. 15.

In this figure, we subtracted the velocity measured when the acoustic field was off, that was 2.14 μm/s higher than the characteristic velocity related to Brownian motion estimated to 1 μm/s.

The latter value was estimated by calculating the diffusion coefficient D=kT/3πηd~5.5×10$^{-9}$ cm$^2$/s where d=800 nm, k is the Boltzmann constant and T the absolute temperature.

The diffusion length l in a time t=1 s given by l=(2Dt)$^{1/2}$ is thus about 1 μm. Remaining currents due to defects in horizontally of the chamber and other thermal effects may account for this minimum streaming.

Figure 15:
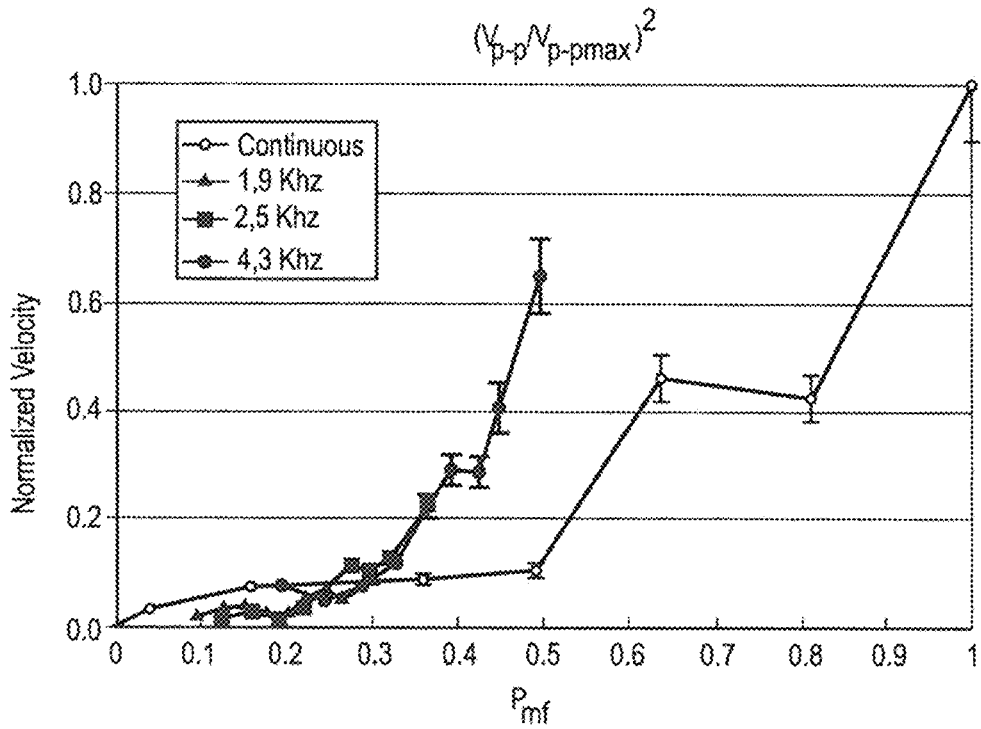
FIG. 15 shows the evolution of the normalized streaming velocity in function of the pulse mode factor (for pulsed mode) and in function of the square of the normalized acoustic amplitude (for continuous mode)

If continuous and pulsed modes were equivalent, curves in FIG. 15 should coincide. We surprisingly find that they diverge as the energy density increases.

It is interesting to analyze the curves corresponding to the pulsed mode. We observe that all points join the same master curve which indicates that $P_{mf}$ is a good parameter for controlling the acoustic streaming.

Nevertheless, the curve that should be linear, according to the assumptions made before, is rather close to a power law. We do not have a clear explanation of this result.

The curve corresponding to the continuous mode can be divided in two parts, one of constant lower values of the streaming velocity and one not clearly linearly increasing as predicted by the theory.

The divergence in both behaviors shows that for generating the same acoustic streaming velocity and ensuring a satisfying acoustic focusing, it is necessary to have less energy in pulsed mode than in continuous mode.

We find this result remarkable because this indicates that pulsed mode seems to be a more efficient way of applying ultrasound in resonators.

Less energy implies also less heat dissipation that is a good advantage when ultrasounds need to be applied for long periods.

Example 3

Observation of the Acoustic Streaming in Function of $P_{mf}$ and $T_p$

A series of experiments aiming to find the conditions in pulsed mode under which the acoustic streaming was reduced to a minimum were performed in the UR1 device.

The procedure was to use continuous mode for focusing the 800 nm latex particles at the nodal plane and generating acoustic streaming. We then switched to pulsed mode and systematically varied the number of pulses and the repetition frequency.

We thus visually determined the conditions at which the streaming stops or is reduced to the minimum observable ($v_s$<2.5 μm/s).

Figure 16:
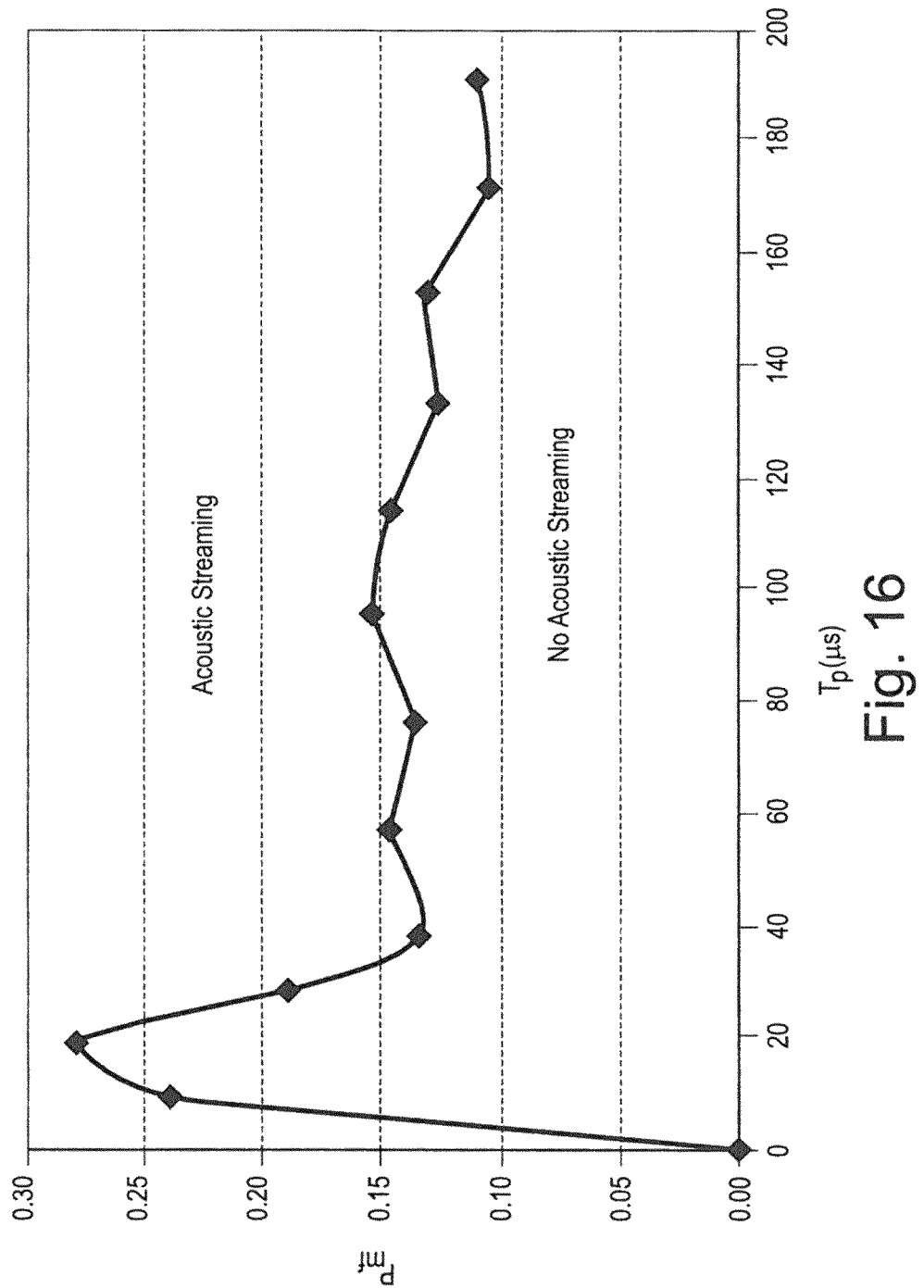
FIG. 16 shows the acoustic streaming threshold obtained in pulsed mode.

In FIG. 16 is depicted a graph showing the values of $P_{mf}$ and $T_p$ which allow the observation of the acoustic streaming. Two regions are highlighted: above the curve the acoustic streaming is observed and under the curve the acoustic streaming is negligible.

Higher values of $T_p$ corresponding in our experiment to 50 pulses per group do not seem to vary too much around an average value $P_{mf}$~0.12. This value depends on the ultrasonic frequency and probably on the geometry of the resonator. Values obtained in the UR2 device, operated at 4.2 MHz, have similar behavior around $P_{mf}$~0.1.

Curve in FIG. 16 may allow the optimization of the parameters to be used in pulsed mode for controlling the streaming.

Example 4

Evidence of Reduction of the Acoustic Streaming without Inhibiting Focusing of Particles It was proven that the acoustic streaming can be efficiently controlled by the pulsed mode of operation.

The results detailed hereunder prove that the pulsed mode of operation is able to reduce the acoustic streaming while keeping the primary and secondary radiation forces strong enough to efficiently manipulate micron-sized and sub-micron-sized particles at the same time.

The capabilities of the resonator to focus particles at the nodal plane in continuous and pulsed modes in conditions of minimum streaming velocity are hereunder compared.

Experiments were conducted with 800 nm latex particles. After the injection of the suspension in the chamber, particles were distributed in the entire thickness in the absence of acoustic field.

After a few seconds, when the suspension reached a stationary state, the acoustic field was applied generating migration of particles towards the node. Measurements of the layer thickness have been done after a relaxation time of 45 s which was the time taken by the suspension to reach the new stationary state.

The layer thickness around the acoustic focusing was roughly estimated by locating the position of the first and the last particles at the focus of the microscope.

In continuous mode, as expected, the layer thickness increased when the wave amplitude decreased. The variations were from 70 to 80 μm at maximum amplitude (13 Vp-p) to 180-190 μm at minimum amplitude (4.2 Vp-p).

Let's recall that the chamber was w=280 μm thick, thus the layer occupied about ~0.7w.

In pulsed mode, at $P_{mf}$~0.15 and at an amplitude of 4.2 Vp-p, when the streaming velocity was minimum, the layer thickness was 100-110 μm thus much smaller than in continuous mode and occupied about ~0.35 w.

This result clearly shows that the primary radiation force is stronger in pulsed mode than in continuous mode. This result is qualitatively in agreement with the result suggested by FIG. 15 i.e stronger acoustic forces are generated in pulsed mode in comparison to continuous mode for equivalent average amplitudes.

In order to test the capability of the resonator to keep primary and secondary radiation forces strong enough for generating particle levitation and aggregation, we performed experiments using a 15 μm and 800 nm mixture of latex particles in the UR2 device. The UR2 device is a cylindrical resonator optimized for generating aggregates at the center.

The first test consisted in operating the resonator in continuous mode to produce an aggregate of 15 μm particles. A sequence of four images where the aggregate in levitation is surrounded by 800 nm colloidal particles is shown in FIGS. 17A to 17D.

Figure 17A:
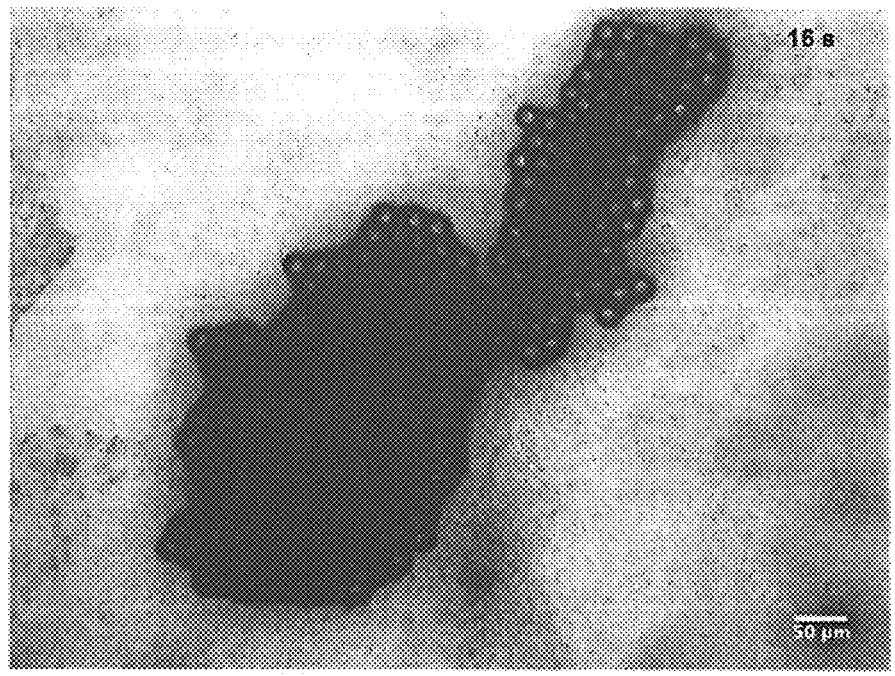
FIGS. 17A to 17D show images of the acoustic streaming observed at the levitation plane in continuous mode (20×) at different times for a mixture of 0.8 and 15 μm latex beads.
Figure 17B:
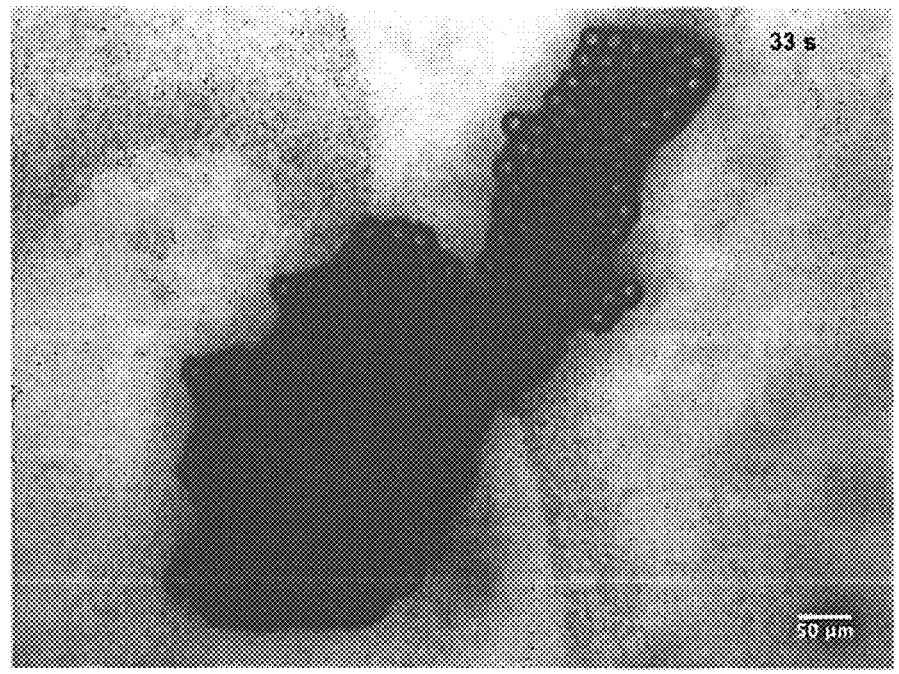

Images in FIGS. 17A and 17B separated of 17 s show the evidence of the coexistence between a stable aggregate and the acoustic streaming. The pattern formed by the smaller particles evolves showing a cloud approaching the aggregate.

Figure 17C:
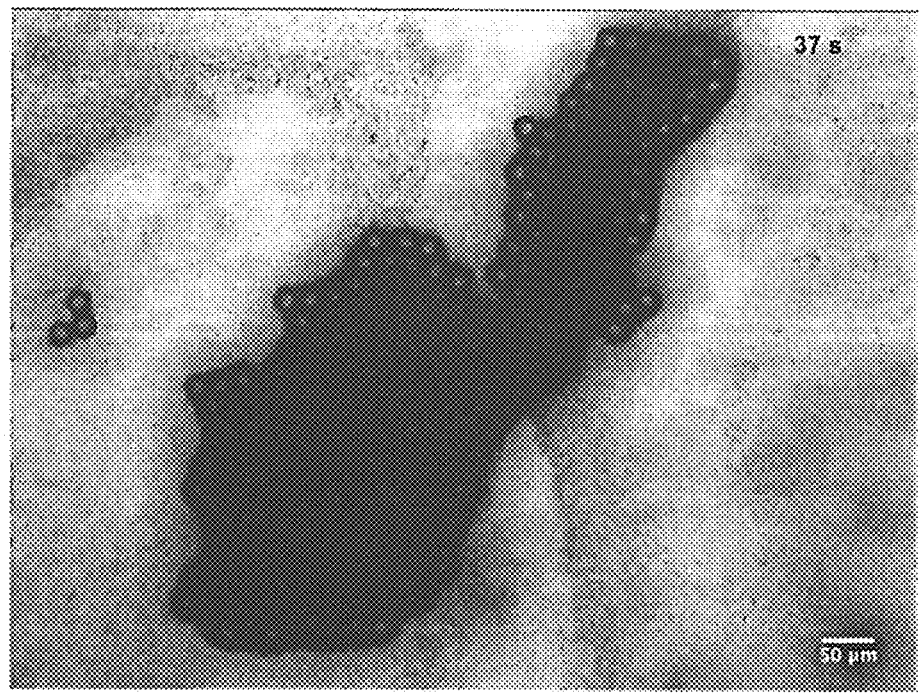
Figure 17D:
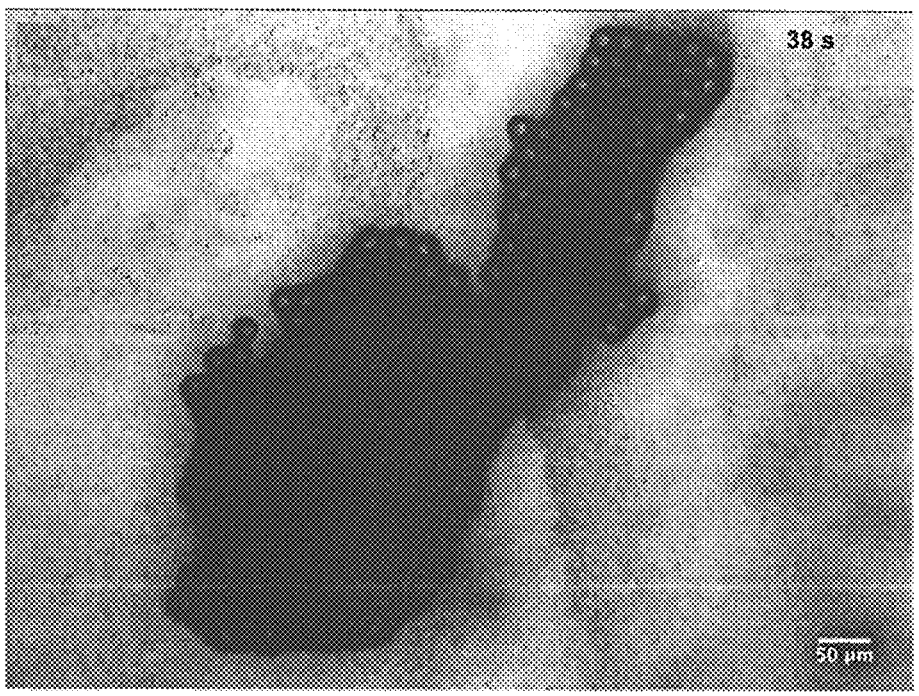

Images in FIGS. 17C and 17D show an aggregate of three particles reaching the main aggregate pushed by secondary radiation forces at a velocity much higher than that of the acoustic streaming. The aggregate is at stable position and is not affected by the streaming.

These experiments showed that if we were interested only in aggregation of micron-sized species, we might neglect the acoustic streaming.

The experiment followed by switching the system to pulsed mode at 100 pulses per group and repetition frequency of 6.5 kHz.

Figure 18A:
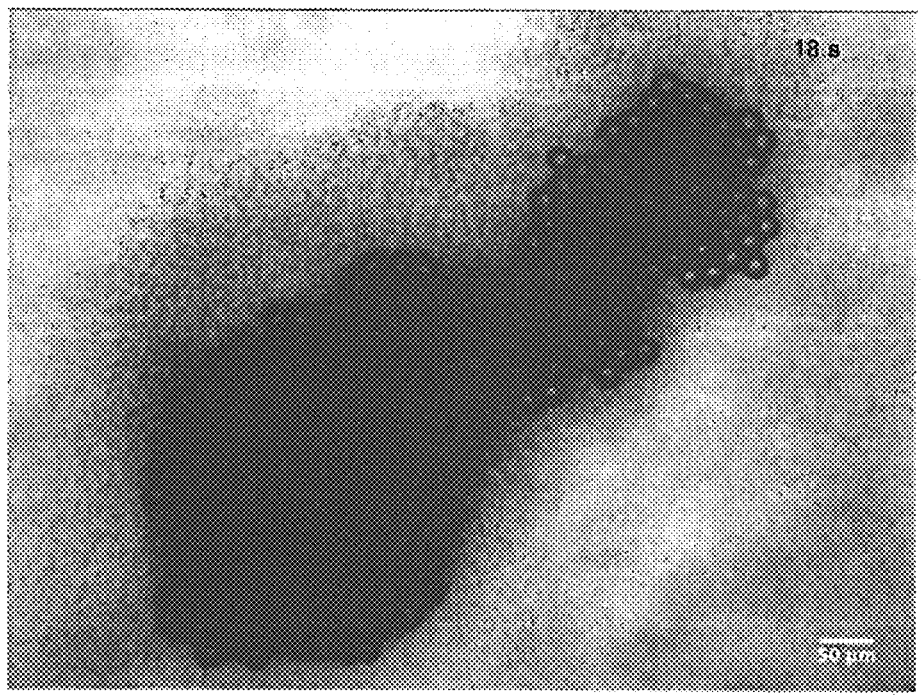
FIGS. 18A and 18B show images of 0.8 μm particles around a 15 μm particle aggregate obtained in pulsed mode at different times (34 s interval) at the levitation plane (20×)
Figure 18B:
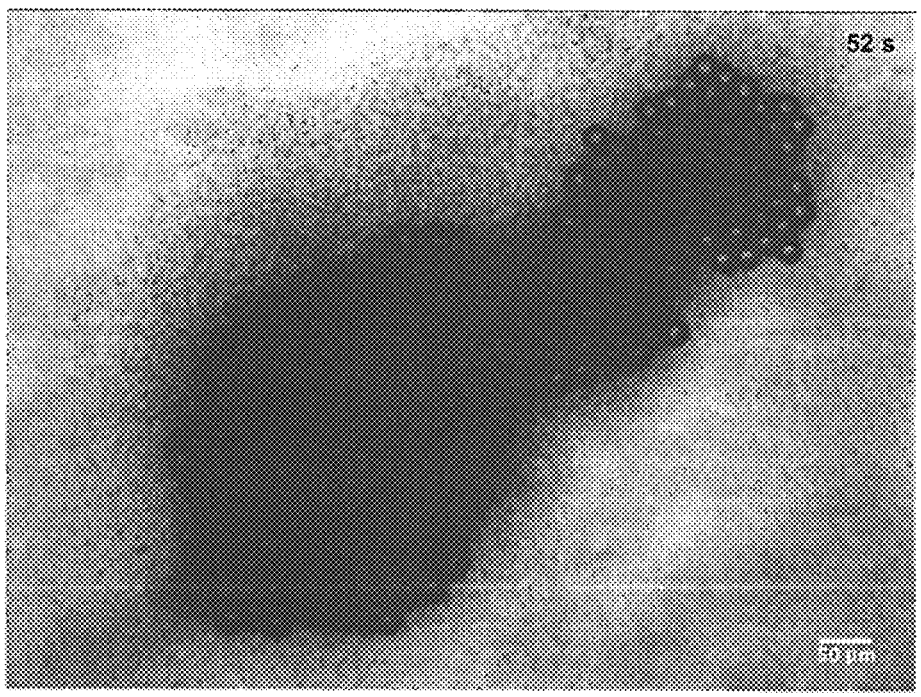

A stationary state is observed in FIGS. 18A and 18B that show images at 34 s time interval. We also observe that the configuration of colloidal particles around the aggregate remains stable, the aggregate was focused at the same plane as in continuous mode.

Analogue experiments performed in continuous mode at the threshold of the streaming showed that the levitation time (i.e. time to reach the levitation plane from the bottom of the resonator) was longer than that in pulsed mode. In this case the levitation time was more than one second and the aggregate did not levitate consolidated as observed in pulsed mode.

This result indicates that primary radiation force is stronger in pulsed mode than in continuous mode as previously stated based on the observation of the particle layer thickness.

The last experiment concerned secondary forces. We measured the velocity of individual 15 μm particles aggregating in continuous and pulsed modes at the threshold of the streaming.

The constant velocity is the result of the equilibrium established between Stokes' drag force and secondary radiation forces responsible of the aggregation at the nodal plane. We measured 5 velocities for each mode and, in average, we found that the velocities in pulsed mode may reach 35 μm/s while in continuous mode the velocities were less than 5 μm/s.

This result clearly demonstrates that secondary forces are also stronger in pulsed mode than in continuous mode.

Finally, we tracked a ~10 μm aggregate of 800 nm particles in pulsed mode at the threshold of the acoustic streaming.

Figure 19:
FIG. 19 shows superimposed images (10×) separated by 7 min of an aggregate of 800 nm particles migrating at the levitation plane in pulsed mode.

FIG. 19 is a superposition of two images separated by 7 min. The velocity of the aggregate was 0.6 μm/s while the velocity of individual particles was ~2.5 μm/s. This relative velocity is related to the acoustic trapping of the aggregate by the acoustic forces.

This result demonstrates that colloidal aggregates could be manipulated by ultrasounds in pulsed mode.

The expression "comprising a/one" should be understood as "comprising at least one".

The expression "comprised between . . . and . . . " should be understood with the end points included.

The invention claimed is:

1. A method of manipulating objects in a channel comprising a liquid, said method comprising:
    a) providing said objects in at least a region of the channel, and
    b) forming a layer of said objects by submitting them to an amplitude modulated pulsed acoustic field.

2. A method according to claim 1, wherein the amplitude modulated pulsed acoustic field comprises a repetition of a plurality of acoustic wave pulse groups, said groups being separated between each other by a period having a non-zero duration wherein no acoustic wave is applied.

3. A method according to claim 1, wherein the amplitude modulated pulsed acoustic field comprises a repetition of a plurality of acoustic wave pulse groups, said groups being separated between each other by a period having a non-zero duration wherein an acoustic wave is applied, said acoustic wave having at least one extremum of the absolute value of its amplitude that is different from the highest amplitude of the acoustic wave pulse(s) belonging to the group just preceding said period.

4. A method according to claim 1, wherein a standing acoustic wave is created along a dimension of the channel at step b) during the application of the amplitude modulated pulsed acoustic field.

5. A method according to claim 1, the amplitude modulated pulsed acoustic field comprising a repetition of a plurality of acoustic wave pulse groups, at least one of the acoustic wave pulse groups comprising 5 or more acoustic wave pulses which have substantially the same amplitude and/or frequency.

6. A method according to claim 1, the amplitude modulated pulsed acoustic field comprising a repetition of a plurality of acoustic wave pulse groups, at least one of the acoustic wave pulse groups lasting a duration $T_p$, that is greater than or equal to 0.1 μs.

7. A method according to claim 1, step b) comprising submitting the objects to at least 50 acoustic wave pulse groups.

8. A method according to claim 1, the amplitude modulated pulsed acoustic field comprising a repetition of a plurality of acoustic wave pulse groups, at least one period separating two successive acoustic wave pulse groups having a duration $T_r$ that is greater than or equal to 0.05 ms and/or that is less than or equal to 0.5 s.

9. A method according to claim 1, at least two couples of consecutive acoustic wave pulse group of duration $T_p$ and period separating two successive acoustic wave pulse groups of duration $T_r$ having a different pulse mode factor $$P_{mf} = \frac{T_p}{T_p + T_r}.$$

10. A method according to claim 1, all the couples of consecutive acoustic wave pulse group of duration and period separating two successive acoustic wave pulse groups of duration $T_r$ having substantially the same pulse mode factor $$P_{mf} = \frac{T_p}{T_p + T_r}.$$

11. A method according to claim 1, the amplitude modulate pulsed acoustic field comprising a repetition of a plurality of acoustic wave pulse groups which are periodically spaced between each other by a period having a non-zero duration.

12. A method according to claim 1, wherein at least a couple of consecutive acoustic wave pulse group of duration $T_p$ and period separating two successive acoustic wave pulse groups of duration $T_r$ has pulse mode factor $$P_{mf} = \frac{T_p}{T_p + T_r}$$

that is greater than Or equal to 0.01 and/or that is less than or equal to 0.95.

13. A method according to claim 1 wherein the layer of objects is focused around a nodal or antinodal plane during all or part of step b).

14. A method according to claim 1, wherein colloidal objects are manipulated and a layer of said colloidal objects is formed during all or part of step b).

15. A method according to claim 14, wherein one or a plurality of colloidal aggregates are manipulated during all or part of step b).

16. A method according to claim 14, wherein a mixture of colloidal objects and non-colloidal objects is manipulated during ail or part of step b).

17. A method according to claim 16, wherein said colloidal and non-colloidal objects are focused around a same nodal or antinodal plane during all or part of step b).

18. A method according to claim 1, wherein the greatest dimension of the layer formed at step b) measured along the axis of application of the acoustic waves is comprised between $50d_{av}$ and $150d_{av}$ where $d_{av}$ is the average size of the objects when not aggregated.

19. A method according to claim 1, wherein the liquid is flowing during step b), the Reynolds number of the flow of the liquid being 10 or less during step b).

20. A method according to claim 1, wherein the amplitude modulated pulsed acoustic field comprises a repetition of a plurality of acoustic wave pulse groups, at least one of said groups consisting in a single acoustic wave pulse.

* * * * *